April 4, 1967 J. C. MIKKELSEN Plant Pat. 2,732
POINSETTIA PLANT
Filed Feb. 25, 1966
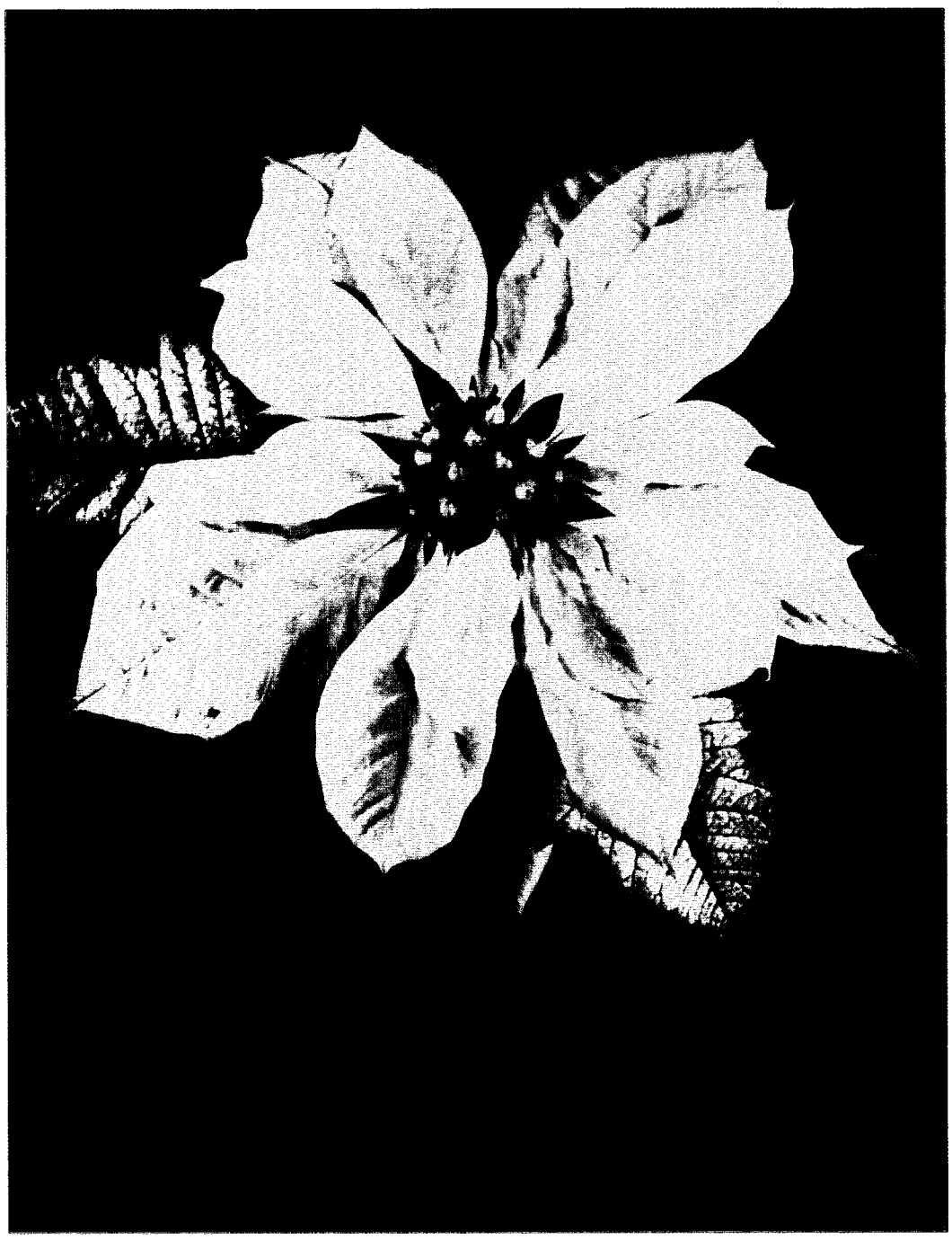
Inventor.
J. C. Mikkelsen
By: Robb & Robb
Attorneys.

United States Patent Office

Plant Pat. 2,732
Patented Apr. 4, 1967

2,732
POINSETTIA PLANT

James C. Mikkelsen, 1803 W. 13th St.,
Ashtabula, Ohio 44004

Filed Feb. 25, 1966, Ser. No. 530,239
1 Claim. (Cl. Plt.—86)

The present invention relates to a new and distinct variety of poinsettia plant which was discovered by me as a mutation of the variety known as "Mikkelpink" (Plant Patent No. 2501) which produced a sport thereof having new and distinct bract characteristics.

In the course of growing the variety "Mikkelpink" under my direction and control in my greenhouses at Ashtabula, Ohio, some of the plants were forced into flower by shortening the photoperiod. Among this group of plants, my attention was attracted to one plant which had produced variegated pink and white bracts. These bracts were then removed and I took several leaf bud cuttings from the plant and propagated the same under mist while subjecting the cuttings to high temperatures and artificial light for controlled periods. Also, several bottom leaf nodes were left on the original plant, and the plant was also subjected to controlled temperature and artificial light for predetermined periods to force out new vegetative growth from which vegetative shoots were taken and propagated to produce stock plants. Some of the leaf bud cuttings were potted and forced into vegetative growth to be added to the stock clones. All of these plants consistently produced the variegated pink and white bracts, thereby conclusively confirming that this unique characteristic comes true by asexual reproduction, as still further established by propagation of cuttings from the stock plants referred to in the foregoing, all as grown by me at Ashtabula, Ohio.

Except for the variegated bract coloring aforesaid, my new poinsettia variety has the same overall general characteristics of the parent variety "Mikkelpink" and achieves the following new and distinct combination of features which are outstanding therein and which distinguish it from all other poinsettia varieties of which I am aware:

(1) A semi-dwarf habit of growth;

(2) Rigid and upright stems which do not require staking and which are ideal for short, compact and long-lasting plants which are particularly suitable for home decorations;

(3) Relatively small flow buds which do not drop excessive pollen or nectar;

(4) Highly decorative, attractive and distinctively colored bracts which have a light cream-white background color overlaid with two shades of pink coloration in irregular areas of varying widths;

(5) A non-drooping habit of the bracts with age;

(6) Excellent keeping qualities without exacting growing techniques to prevent early flowering; and (7) Good shipping qualities attributable to the semi-dwarf habit, rigid stems and short leaves and bracts which are less susceptible to damage or injury during shipping than most other commercial varieties.

The accompanying drawing shows a typical specimen plant of my new poinsettia variety as depicted in color as nearly true as it is reasonably possible to make the same in a color illustration of this character.

The following is a detailed description of my new poinsettia variety, with color terminology in accordance with Wilson's Horticultural Colour Chart, except where general color terms of ordinary dictionary significance are obvious, as based on specimens grown at Ashtabula, Ohio, under regular commercial practices:

Parentage: Sport of "Minkkelpink."

Form: Semi-dwarf; compact; upright; no branching.

Habit of growth: Slower than present commercial varieties; no self-branching.

Rooting habit: Substantially identical to that of the antecedent variety "Paul Mikkelsen" (Plant Patent No. 2,328); roots are quite fibrous and less susceptible to root rot organisms than present commercial varieties, as determined by comparison with other varieties grown under comparable conditions at Ashtabula, Ohio.

Blooming habit: Normal.

Blooming season: Late November and December; very suitable for forcing.

Foliage: Alternate on stems; borne on stems at a slight upward angle ranging from about 15° to 20°; foliage does not tend to fall off as the plant matures or when subjected to sudden environmental changes.

*Size.*—Medium (from about 4 inches to 6 inches long) when grown with good fertilizing practices.

*Quantity.*—Above normal.

*Shape.*—Indented and pointed (short and stubby pointed with oak leaf pattern).

*Texture.*—Upper side—becomes semi-glossy at maturity; veins have definite recessed and dendritic pattern. Under side—dull; veins have definite protrusion.

*Margin.*—Clean-cut and distinct.

*Color.*—New foliage—upper side: Sap Green, Plate 62, page 62, when about ½ inch to ¾ inch long, changing to Pod Green, Plate 061, page 120 when about 2 inches to 3 inches long. Under side: Pod Green, Plate 061, page 120. Old foliage—upper side: Spinach Green, Plate 0960, page 187. Under side: Spinach Green, Plate 0960/2, page 187. Petiole—Color: Light Green and has no Pink coloration as in "Mikkelpink" or Red coloration as in "Paul Mikkelsen."

Disease resistance: Resistant to botrytis and mildew, as determined by comparison with other varieties grown under the same cultural conditions at Ashtabula, Ohio, which were infected with these diseases.

Bracts: Become more long-pointed as cyathia develop; bract development continues over a period of time and bracts retain a horizontal position for many months; bracts have a slight twisting formation at the very tip end.

*Color.*—White background color, overlaid with two shades of Pink similar to the Camellia Rose, Plate 622/1, coloring of "Mikkelpink," with the overlay superimposed over the background and over each other in separate layers of pigmented cells, creating three irregular but distinct color zones from very thin areas to about ½ inch to ¾ inch or more wide, with the pink colorations varying in intensity according to light and temperature conditions.

Flowers:

*Borne.*—Continuously for several months, with many cyathia to a stem in regular clusters in varying stages of development; borne on short, strong stems.

*Quantity of bloom.*—Relatively abundant; continuous during one season of 3 to 4 months.

*Cyathia.*—Small; borne on Light Green stems corresponding to the same color as the main stem of the plant in that area; cyathia drop off gradually after maturity, but new ones continue to develop as the flowering stems continue to develop. Color—Scheele's Green, Plate 860/1, page 175, with the outer areas of the cyathia turning to Lemon Yellow, Plate 4/1, page 4, instead of Red as in the "Paul Mikkelsen" and "Mikkelpink" varieties and constituting a significant difference.

Reproductive organs:

*Stamens.*—Quite numerous; from ⅛ to ¼ inch long. Color—colorless in early stages, but turning to Cream-White when stamens drop.

*Pollen.*—Color—Canary Yellow, Plate 2, page 2.

*Styles.*—Color—Cream-White, turning to Pinkish or dirty White at maturity.

*Ovaries.*—Color—Scheele's Green, Plate 860/1, page 175.

*Nectar cups.*—Color—Lemon Yellow, Plate 4/1, page 4.

*General observations*

My new variety is a significant contribution to the poinsettia industry in that it adds a unique and novelty type having the same over-all characteristics as the varieties "Paul Mikkelsen" and "Mikkelpink," and allowing growers to have the full range of colors growing under the same cultural conditions.

I claim:

A new and distinct variety of poinsettia plant, substantially as herein shown and described, characterized particularly as to novelty by the unique combination of a semi-dwarf habit of growth, rigid and upright stems which do not require staking and which are ideal for short, compact and long-lasting plants which are particularly suitable for home decorations, relatively small flower buds which do not drop excessive pollen or nectar, highly decorative, attractive and distinctively colored bracts which have a light cream-white background color overlaid with two shades of pink coloration in irregular areas of varying widths, a non-drooping habit of the bracts with age, excellent keeping qualities without exacting growing techniques to prevent early flowering, and good shipping qualities attributable to the semi-dwarf habit, rigid stems and short leaves and bracts which are less susceptible to damage or injury during shipping than most other commercial varieties.

No references cited.

ABRAHAM G. STONE, *Primary Examiner.*

ROBERT E. BAGWILL, *Examiner.*